(12) United States Patent
Tachibana et al.

(10) Patent No.: US 6,332,095 B1
(45) Date of Patent: *Dec. 18, 2001

(54) METHOD OF EXCITING PHOTOSENSITIVE MATERIAL

(76) Inventors: Katsuro Tachibana, 6-18, Kusagae 1-chome, Chuou-ku, Fukuoka-shi Fukuoka 810-0045; Toshiki Uchida, Room 303, 20-17, Hoshikuma 2-chome, Jounan-ku, Fukuoka-shi, Fukuoka 814-0132, both of (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/180,812

(22) PCT Filed: Mar. 30, 1998

(86) PCT No.: PCT/JP98/01450

§ 371 Date: Nov. 16, 1998

§ 102(e) Date: Nov. 16, 1998

(87) PCT Pub. No.: WO98/43671

PCT Pub. Date: Oct. 8, 1998

(30) Foreign Application Priority Data

Mar. 31, 1997 (JP) .................................................. 9-081505

(51) Int. Cl.⁷ ........................................................ A61N 1/30
(52) U.S. Cl. ............................................... 604/20; 604/500
(58) Field of Search ................................ 604/4–6, 20, 21, 604/500, 22; 600/9, 13–15; 607/1–3, 115; 128/897, 898

(56) References Cited

U.S. PATENT DOCUMENTS

| | | | |
|---|---|---|---|
| 4,614,190 | * | 9/1986 | Stanco et al. ........................ 128/395 |
| 5,211,622 | * | 5/1993 | Liboff et al. ............................ 600/9 |
| 5,225,433 | * | 7/1993 | Dougherty et al. .................. 514/410 |
| 5,489,590 | * | 2/1996 | Gulliya et al. .................... 514/224.8 |
| 5,599,923 | * | 2/1997 | Sessler et al. ....................... 540/145 |
| 5,773,460 | * | 6/1998 | Gaboury et al. ..................... 514/454 |
| 5,776,925 | * | 7/1998 | Young et al. ........................ 514/185 |
| 5,944,748 | * | 8/1999 | Mager et al. .......................... 607/88 |

* cited by examiner

Primary Examiner—Sharon Kennedy
(74) Attorney, Agent, or Firm—Jordan and Hamburg LLP

(57) ABSTRACT

A method of treating abnormal cells, including cancer cells, includes administering a photosensitive chemical substance to accumulate at the cancer cell and applying a constant electric field or a high frequency electric field to the abnormal cells to thereby excite the photosensitive chemical substance to undergo a reaction detrimental to the abnormal cells. The abnormal cells may be in tissues inaccessible to light, including cancer cells in the blood.

16 Claims, 2 Drawing Sheets

METHOD OF EXCITING PHOTOSENSITIVE MATERIAL

BACKGROUND OF THE INVENTION

Technical Field

The present invention relates to a method of exciting photosensitive materials and, more particularly, to a method of exciting photosensitive substances in producing therapeutic effects by causing the photochemical substances to accumulate on or in various cancer cells or cancer tissues, or abnormal cells or abnormal tissues and exciting the photosensitive substances that have accumulated, to thereby kill or damage the cancer cells, cancer tissues and so on.

The use of photosensitive substances for selectively killing or damaging various cancer cells or cancer tissues is known. The photosensitive substances accumulate on or in various cancer cells or cancer tissues, or abnormal cells or abnormal tissues and then, upon excitation generally with visible rays such as laser beams, they undergo chemical reactions and kill or damage various cancer cells or cancer tissues more specifically than normal tissues to thereby produce therapeutic effects.

On the occasion of treatment, a photosensitive substance is systemically administered and then the photosensitive substance is excited endoscopically with laser beams in the case of cancer or carcinoma of the stomach, esophagus, lung, larynx and pharynx, uterine cervix, bladder or the like, or directly with laser beams in the case of cancer or carcinoma on the body surface, for example skin cancer.

When, according to the prior art, light is used as the energy source for excitation, the range of killing and damaging effects or therapeutic effects depends on the extent of tissue penetration of visible rays such as laser beams, and the maximum penetration is said to be about 1.5 cm. Therefore, the effects can be produced only on superficial lesions, in particular early carcinomas, and the range of application is restricted.

Excitation with light is effective only against localized lesions and is quite incapable of bringing about complete recovery in patients with metastatic cancer.

In the case of excitation with light, a long period of irradiation, generally scores of minutes, is required for attaining satisfactory effects.

In the case of using a photosensitive substance for removing cancer cells in blood by extracorporeal circulation or for removing minute cancer cells remaining in autologous bone marrow transplants (purging), the use of light for excitation can hardly result in successful excitation since the light is blocked by erythrocytes contained therein.

Under the existing circumstances, as mentioned above, light irradiation has its limits against cancer cells in the depth of tissues, which light cannot reach, or in blood, and its range of application is limited to those sites which involve superficial lesions that can be confirmed visually and can be irradiated with light. Another problem is that a long period of time is generally required for light irradiation.

On the other hand, irradiation with ultrasonic waves in lieu of light has been proposed, as described in Uchida et al. "Effects of acoustochemical therapy using porfimor sodium on adult T cell leukemia cells", Jpn Med Ultrasonic, Vol. 23, No. 9 (1996), pp. 23–28.

However, the excitation with ultrasonic waves has the following problems.

Since ultrasonic waves are very poor in propagation efficiency in the air, it is difficult to apply them to digestive tracts, lungs and the like, which have lumina or cavities. Further, since ultrasonic waves are to be used in contact with the target, it is difficult to irradiate a wide range, for example over the whole body, therewith. In addition, since ultrasonic waves can hardly permeate bone portions, it is difficult to irradiate the inside of bones therewith.

Accordingly, it is an object of the present invention to efficiently excite photochemical substances against cancer lesions in the depth of tissues, which are unaccessible by light or ultrasonic waves, or against cancer cells in blood.

SUMMARY OF INVENTION

The present invention is characterized in that a direct current electric field or high-frequency waves are applied to photosensitive substances or photochemical substances, that have accumulated on or in various cancer cells or cancer tissues, or abnormal cells or abnormal tissues, to thereby excite the photochemical substances and cause them to undergo a chemical reaction or reactions.

The present invention is also characterized in that the high-frequency waves mentioned above are generated by using a Tesla coil.

The present invention includes in a method of efficiently exciting photochemical substances against cancer lesions in the depth of tissues, which are unaccessible to light, or against cancer cells in blood.

So far it has been considered that photosensitive substances can be activated only by light. As a result of experiments made by the present inventors under various conditions, however, it was found that they can be activated by a direct current electric field or high-frequency waves as well. Based on this finding, photosensitive substances are activated by a direct current electric field or high-frequency waves in the present invention.

Direct currents, or high-frequency waves such as microwaves or radio waves can readily permeate tissues, hence can sufficiently excite photosensitive substances against cancer cells unaccessible to light. Further, the irradiation possibility range can be markedly expanded, and the treatment of metastatic cancer foci also becomes possible by whole body irradiation. Furthermore, direct currents, or microwaves or radio waves can efficiently reach the depth of tissues as compared with light, so that satisfactory killing or damaging effects can be obtained by a short period of irradiation.

DETAILED DESCRIPTION

Figure 1:
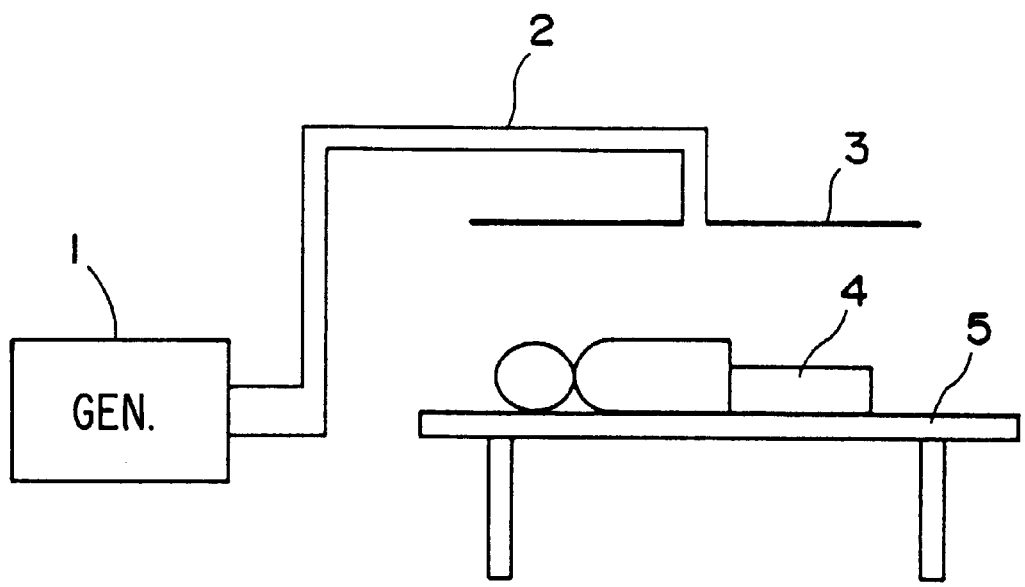
FIG. 1 is a diagram showing an example of a mode of application of a method of exciting photosensitive substances as provided by the present invention.

FIG. 1 is a diagram showing an example, of a mode of application of a method of exciting photosensitive chemical substances as provided by the present invention. The output of an electromagnetic energy generator 1, which generates electromagnetic energy with a predetermined frequency, is supplied, via a feeder 2, to an antenna 3. The antenna 3 is disposed above a treatment bed 5 on which a patient 4 to be treated lies.

The above-mentioned electromagnetic energy generator 1 generates electromagnetic energy with a frequency, for example, within the range of several tens of kHZ to several million kHz. To use a Tesla coil as the electromagnetic energy generator 1 is desirable. This is because the signals generated by a Tesla coil are high-voltage but weak-current ones, hence less dangerous. If an electric current should flows through a human body, it flows on the body surface owing to the skin effect because of its comprising high-frequency waves, hence the danger is slight.

Figure 2:
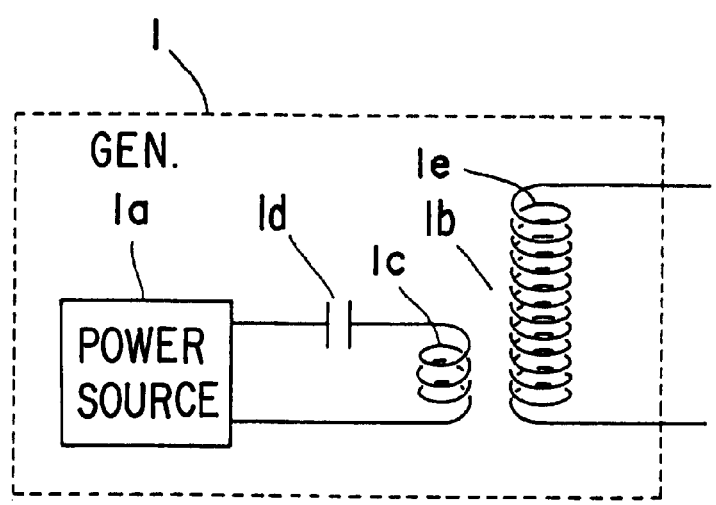
FIG. 2 is a schematic representation of a construction example of an electromagnetic energy generator 1 in which a Tesla coil is used.

FIG. 2 is a schematic representation of a construction example of an electromagnetic energy generator 1 in which a Tesla coil is used. The output of an intermittent power source 1a, which is intermittent at a relatively low frequency, for example, the commercial power source frequency of 50 Hz or 60 Hz, is supplied to a series circuit of a Tesla coil 1b, which comprises a primary winding 1c and a capacitor 1d. Since the electric current flowing through this series circuit is intermittent at a relatively low frequency, an oscillating current having a resonance frequency determined by the inductance of the primary winding 1c and the capacity of the capacitor 1d of the Tesla coil 1b, for example several MHz, flows through the primary winding 1c of the Tesla coil at each occasion of intermittence. The frequency is not limited to that mentioned above and includes frequencies within the range of 1,000 Hz to 5 GHz may be used.

The voltage generated in the primary winding 1c is stepped up according to the turn ratio between the primary winding 1c and secondary winding 1e. Therefore, the secondary winding 1e of the Tesla coil 1b emits high-frequency high-voltage signals. The output of the secondary winding 1e of the Tesla coil 1b is supplied to the antenna 3, and 100 W electromagnetic waves, for instance, are emitted. The patient 4 is irradiated with the electromagnetic waves emitted from the antenna 3.

The patient 4 has been administered beforehand with a photosensitive substance. The photosensitive substance may be selected from among porfimor sodium (trademark: Photofrin), Merocyanine 540 (trademark), ATX-70 (trademark), photoexcitable fullerenes and titanium oxide, for instance.

The photosensitive substance is irradiated, through the skin and intracorporeal tissues of the patient 4, with the electromagnetic waves emitted from the antenna 3, and the photosensitive substance is activated. Therefore, the photosensitive substance can be excited to a sufficient extent against cancer cells unaccessible to light. Further, the irradiation possibility range can be markedly expanded, and the treatment of metastatic cancer foci also becomes possible by whole body irradiation.

Figure 3:
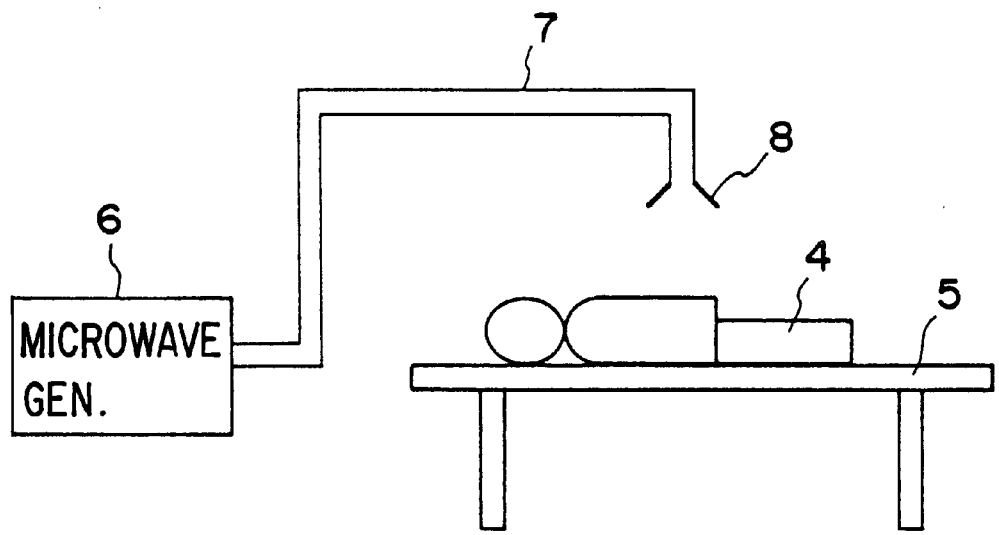
FIG. 3 is a diagram showing an example of the mode of application of the method of exciting photosensitive substances as provided by the present invention, in which microwaves are used as the electromagnetic waves.

FIG. 3 is a diagram showing an example of a mode of application of a method of exciting photosensitive substances as provided by the present invention, in which microwaves are used as the electromagnetic waves.

In a microwave generating circuit 6, microwaves with a wavelength of about 1 to $10_{-4}$ meter are generated. These microwaves are supplied, via a waveguide 7, to an antenna 8 of the horn type, for instance, and the microwaves are emitted from the antenna 8. The patient 4 is irradiated with the electromagnetic waves emitted from the antenna 8. In this case, too, the same effects as in the example illustrated in FIG. 2 can be obtained.

Figure 4:
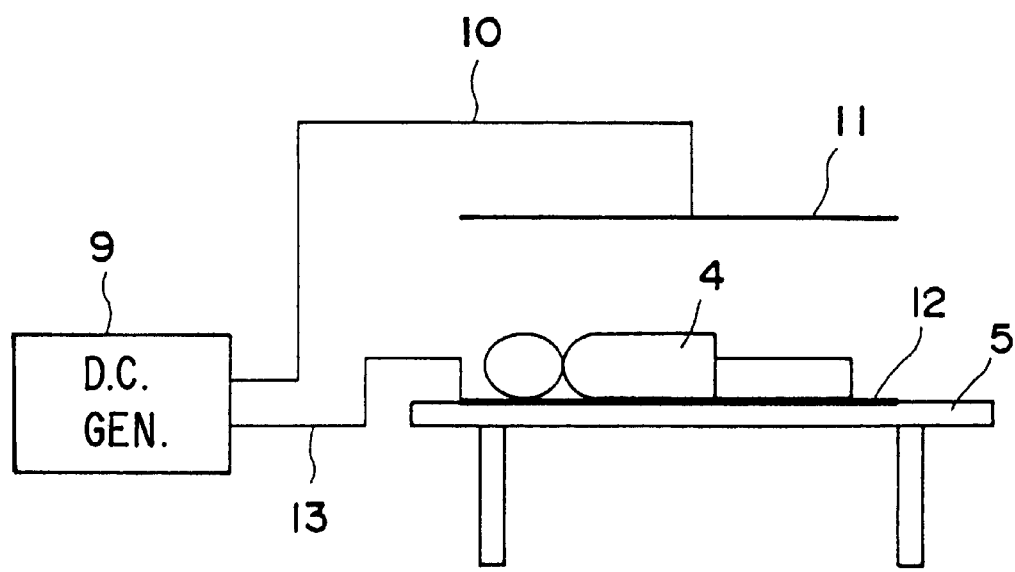
FIG. 4 is a diagram showing an example of a mode of application of a method of exciting photosensitive substances as provided by the present invention, in which an electric field is used.

FIG. 4 is a diagram showing an example of a mode of application of a method of exciting photosensitive substances as provided by the present invention, in which an electric field is used. In the example shown in FIG. 4, a direct-current high voltage of 30 kV, for instance, is generated in a direct-current voltage generating circuit 9 and this high voltage is transmitted, via a lead wire 10, to a field-applying electrode 11 disposed above the treatment bed 5. The treatment bed 5 is provided with an earthing electrode 12, and this earthing electrode 12 is connected, via a lead wire 13, to a ground voltage portion of the direct-current voltage generating circuit 9.

In the example shown in FIG. 4, a voltage is applied between the field-applying electrode 11 and earthing electrode 12, whereby an electric field is applied to the patient 4 and the photosensitive substance within the body is activated by the electric field.

In the above examples, the photosensitive substance is used singly. It is also possible, however, to in combination use an antitumor agent, for example, the alkylating agent melphalan, the metabolic antagonist methothrexate, the anticancer antibiotic daunorubicin or the like.

As regards the abnormal cells, specific killing or damaging effects can be expected on virus-infected cells, for example cells infected with adult T cell leukemia virus, AIDS virus or the like. Killing and damaging of viruses themselves by a direct action thereon can also be expected.

EXAMPLE

A Tesla coil was constructed by winding a coil of about 500 turns with the vertical direction as its axis. This Tesla coil has a truncated cone form with a lowest end diameter of 100 mm, an upper end diameter of 40 mm and an axial length of 220 mm. A 5-cc container made of a synthetic resin was mounted on the top of this Tesla coil, and 10 g of abnormal cells were placed in this container, together with 20 g of ice. The Tesla coil was then driven at 2 MHz and 100 W for emission of radio waves from the Tesla coil. The cells were irradiated with the radio waves from the Tesla coil for 30 minutes, and the respective survival rates were compared with that of the control group.

With porfimor sodium alone, no cytocidal effects were produced and no changes were found. With the radio waves alone, the survival rate was 95±3.1%. The combined use of porfimor sodium and the radio waves a lowered the survival rate to 65±5.8%. This indicates that porfimor sodium was excited by the radio waves to cause specific cell deaths. On that occasion, no temperature increase was observed.

Microwaves and radio waves can readily permeate tissues, hence can excite photosensitive substances to a sufficient extent against cancer cells unaccessible by light. Further, the irradiation possibility range can be markedly expanded, and the treatment of metastatic cancer foci also becomes possible by whole body irradiation.

Furthermore, direct currents, or microwaves or radio waves can efficiently reach the depth of tissues as compared with light, so that satisfactory killing or damaging effects can be obtained by a short period of irradiation.

What is claimed is:

1. A method of treatment of abnormal cells, including cancer cells, using a photosensitive chemical substance, comprising the steps of:

administering therapeutic amounts of the photosensitive chemical substance in an unexcited state, which is excitable by an electric field, such that the photosensitive chemical substance accumulates at sites of the abnormal cells; and applying radiation at a frequency within a frequency range of radio frequencies through microwave frequencies to the abnormal cells to thereby excite the photosensitive chemical substance to cause a chemical reaction detrimental to the abnormal cells.

2. The method according to claim 1, wherein the radiation is generated using a Tesla coil.

3. The method of claim 2 wherein said photosentive chemical substance is selected from the group consisting of porfimor sodium, Merocyanine 540, ATX70, photoexcitable fullerenes and titanium oxide.

4. The method of claim 3 wherein said photosensitive chemical substance is administered in combination with an antitumor agent.

5. The method of claim 4 wherein said antitumor agent is selected from the group consisting of melphalan, methothrexate, and daunorubicin.

6. The method of claim 1 wherein said photosentive chemical substance is selected from the group consisting of porfimor sodium, Merocyanine 540, ATX-70, photosensitive fullerenes and titanium oxide.

7. The method of claim 6 wherein said photosensitive chemical substance is administered in combination with antitumor agent.

8. The method of claim 7 wherein said antitumor agent is selected from the group consisting of melphalan, methothrexate, and daunorubicin.

9. A method of treatment of abnormal cells, including cancer cells, using a photosensitive chemical substance, comprising the steps of:

administering therapeutic amounts of the photosensitive chemical substance in an unexcited state, which is excitable by an electric field, such that the photosensitive chemical substance accumulates at sites of the abnormal cells; and applying a static electric field to thereby excite the photosensitive chemical substance to cause a chemical reaction detrimental to the abnormal cells.

10. The method of claim 9 wherein said photosensitive chemical substance is selected from the group consisting of porfimor sodium, Merocyanine 540, ATX-70, photoexcitable fullerenes and titanium oxide.

11. The method of 10 claim wherein said photosensitive chemical substance is administered in combination with an antitumor agent.

12. The method of claim 11 wherein said antitumor agent is selected from the group consisting of melphalan, methothrexate, and daunorubicin.

13. A method of treatment of abnormal cells, including cancer cells, using a photosensitive chemical substance, comprising the steps of:

administering therapeutic amounts of the photosensitive chemical substance in an unexcited state, which is excitable by an electric field, such that the photosensitive chemical substance accumulates at sites of the abnormal cells; and applying radiation at a frequency within a frequency range of 1000 Hz to 5 GHz to the abnormal cells to thereby excite the photosensitive chemical substance to cause a chemical reaction detrimental to the abnormal cells.

14. The method of claim 13 wherein said photosensitive chemical substance is selected from the group consisting of porfimor sodium, Merocyanine 540, ATX-70, photoexcitable fullerenes and titanium oxide.

15. The method of claim 14 wherein said photosensitive chemical substance is administered in combination with an antitumor agent.

16. The method of claim 15 wherein said antitumor agent is selected from the group consisting of melphalan, methothrexate, and daunorubicin.

* * * * *